US010485808B2

(12) United States Patent
Schultze-Mosgau et al.

(10) Patent No.: US 10,485,808 B2
(45) Date of Patent: Nov. 26, 2019

(54) SELECTIVE PROGESTERONE RECEPTOR MODULATORS (SPRM) AND STABILIZED ESTROGEN LEVEL IN PATIENT

(71) Applicant: BAYER PHARMA AKTIENGESELLSCHAFT, Berlin (DE)

(72) Inventors: Marcus-Hillert Schultze-Mosgau, Nordbahn (DE); Xinying Chang, Berlin (DE); Christian Seitz, Zeuthen (DE); Carsten Möller, Berlin (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 15/942,802

(22) Filed: Apr. 2, 2018

(65) Prior Publication Data
US 2018/0369257 A1 Dec. 27, 2018

(30) Foreign Application Priority Data

Apr. 3, 2017 (EP) .................... 17164666

(51) Int. Cl.
*A61K 31/567* (2006.01)
*A61K 38/09* (2006.01)
*A61K 31/505* (2006.01)
*A61K 31/57* (2006.01)
*A61P 15/00* (2006.01)
*A61P 5/34* (2006.01)
*A61P 15/12* (2006.01)
*A61P 5/36* (2006.01)
*A61K 31/095* (2006.01)
*A61K 31/573* (2006.01)
*C07J 31/00* (2006.01)

(52) U.S. Cl.
CPC .......... *A61K 31/567* (2013.01); *A61K 31/095* (2013.01); *A61K 31/505* (2013.01); *A61K 31/57* (2013.01); *A61K 31/573* (2013.01); *A61K 38/09* (2013.01); *A61P 5/36* (2018.01); *A61P 15/12* (2018.01); *C07J 31/003* (2013.01)

(58) Field of Classification Search
CPC ........................................................................
61K 31/567; A61K 31/095; A61K 31/505; A61K 31/57; A61K 31/573; A61K 38/09; A61P 5/36; A61P 5/34; A61P 15/00; A61P 15/12
USPC ...................................... 514/230.5
See application file for complete search history.

(56) References Cited

U.S. PATENT DOCUMENTS 8,278,469 B2* 10/2012 Schwede ................ C07J 31/006
552/648
2018/0155388 A1* 6/2018 Seitz .................... A61K 31/567

FOREIGN PATENT DOCUMENTS

EP 3214092 A1 9/2017
WO 2014166971 A1 10/2014
WO 2016184863 A1 11/2016

OTHER PUBLICATIONS

West, Anthony R,, "Solid State Chemistry and its Applications", Wiley, New York, 1988, Chapter 10 (Year: 1988).*
Berge et al., "Pharmaceutical Salts", Journal of Pharmaceutical Sciences, vol. 66, No. 1, Jan. 1977, pp. 1-19.
Biglia et al., "Ulipristal Acetate: A Novel Pharmacological Approach for the Treatment of Uterine Fibroids", Drug Design, Development and Therapy, vol. 8, 2014, pp. 285-292.
Bradley et al., "O-235 Results of the Asteroid (Assess Safety and Efficacy of Vilaprisan in Patients with Uterine Fibroids) 1 Study: A Phase 2, Placebo-Controlled Dose Finding Study", Fertility & Sterility ASRM Abstracts, vol. 106, No. 3, Supplement, Sep. 2016, pp. e95-e96.
Donnez et al., "Ulipristal Acetate versus Leuprolide Acetate for Uterine Fibroids", The New England Journal of Medicine, vol. 366, No. 5, Feb. 2, 2012, pp. 421-432.
Powell et al., "Esmya and the PEARL Studies: A Review", Women's Health, Review 1-5, 2017, 5 pages.
Schütt et al., "Pharmacodynamics and Safety of the Novel Selective Progesterone Receptor Modulator Vilaprisan: A Double-Blind, Randomized, Placebo-Controlled Phase 1 Trial in Healthy Women", Human Reproduction, vol. 31, No. 8, 2016, pp. 1703-1712.
Seitz et al., "Rationale and Design of ASTEROID 2, a Randomized, Placebo- and Active Comparator-Controlled Study to Assess the Efficacy and Safety of Vilaprisan in Patients with Uterine Fibroids", Contemporary Clinical Trials, vol. 55, 2017, pp. 56-62.
Biglia, Nicoletta, et al., "Ulipristal acetate: a novel pharmacological approach for the treatment of uterine fibroids," Drug Design, Development and Therapy, (2014), vol. 8, 285-292.

* cited by examiner

*Primary Examiner* — Yevgeny Valenrod
(74) *Attorney, Agent, or Firm* — McBee Moore Woodward & Vanik IP, LLC

(57) ABSTRACT

The present invention is related to Selective Progesterone Receptor Modulators (SPRM) as described and defined herein, and covers the use of said compounds for manufacturing pharmaceutical compositions for the treatment or prophylaxis of sexual hormone dependent diseases and gynaecological diseases in particular Endometriosis or Uterine Fibroids (UF), as a sole agent or in combination with other active ingredients wherein circulating endogenous estradiol concentration of treated women is maintained to a level in a range of 40 pg/mL to 85 pg/mL.

20 Claims, 3 Drawing Sheets

SELECTIVE PROGESTERONE RECEPTOR MODULATORS (SPRM) AND STABILIZED ESTROGEN LEVEL IN PATIENT

This application claims priority to EP Patent Application No. 17164666.4 filed 3 Apr. 2017, the entire contents of which is hereby incorporated by reference.

The present invention is related to Selective Progesterone Receptor Modulators (SPRM) as described and defined herein, and covers the use of said compounds for manufacturing pharmaceutical compositions for the treatment or prophylaxis of sexual hormone dependent diseases and gynaecological diseases in particular, Endometriosis or Uterine Fibroids (UF), as a sole agent or in combination with other active ingredients wherein circulating endogenous estrogen concentration of treated women is maintained to a level in a range of 40 pg/mL to 85 pg/mL.

BACKGROUND

The present invention is related to Selective Progesterone Receptor Modulators (SPRM) defined as (11β,17β)-17-Hydroxy-11-[4-(methylsulphonyl)phenyl]-17-(pentafluoroethyl)estra-4,9-dien-3-one (Compound 1) of formula (I)

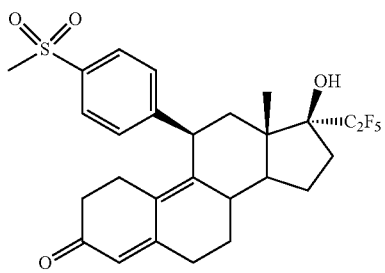

(I)

or a stereoisomer, a tautomer, a hydrate, a solvate, or a salt thereof, or a mixture of same. The said SPRM are disclosed in WO2011/009531A1 which are potent Progesterone Receptor antagonist.

PRIOR ART

The frequency of Uterine Fibroids (UF) in the general population is difficult to quantify because many women with UF are asymptomatic. Ultrasound examination of over 1000 randomly selected members of an urban health plan in the USA has demonstrated that approximately half of premenopausal women with no previous diagnosis of UF had evidence of UF. Heavy menstrual bleeding (HMB) is one of the most common symptoms of UF. Other symptoms of UF may include bulk symptoms such as urinary incontinence/retention, bowel disturbance and pain.

Ulipristal acetate (Esmya®) is a synthetic Selective Progesterone Receptor Modulator that has predominantly inhibitory effects on the progesterone receptor that is currently marketed in Europe for treatment of UF with a dosage of 5 mg/day. It was shown in PEARL II study that Ulipristal acetate alleviates associated symptoms such as menorrhagia or as a pre-treatment to assist with surgical removal of Uterine Fibroids (UF). However, it appears that there are a certain proportion of patients experiencing moderate to severe hot flushes during treatment (not after the return of uterine menses), see Powell et al. Womens Health Review 1-5, 2017.

Moderate to severe hot flushes were perceived to be experienced by 11%, and 10% of patients, receiving 5 mg/day or 10 mg/day of Ulipristal acetate during 12-13 weeks of treatment, respectively. Overall, hot flushes of any severity occurred in 26% (5 mg) and 24% (10 mg). Further, the serum estradiol levels decreased to 64 and 61 pg/mL, respectively after the 12-13 weeks treatment resulting in a low level of estradiol. Finally, amenorrhoea that was taken as secondary endpoint, was achieved with a rate of 75% and 89%, respectively, see Powell et al. Womens Health Review 1-5, 2017. PEARL II results were as well discussed in Donnez et al, The new England Journal of Medicine, 366; 5, February 2010, 421.

Following the cessation of menstruation during the time preceding (perimenopause) and in the menopause (postmenopause), endogenous estrogen concentrations typically decline rapidly. As a consequence various physiological changes may result, including vulvar and vaginal atrophy causing vaginal dryness, pruritus and dyspareunia, and vasomotor instability manifested as hot flushes. The long-term physiological effects of postmenopausal estrogen deprivation may result in significant morbidity and mortality due to increase in the risk factors for cardiovascular disease and osteoporosis. As well, a decrease in endogenous estrogen concentrations may affect negatively bone mass of both cortical (spine) and trabecular (hip) bone.

Estrogen replacement therapy (ERT) is beneficial for symptomatic relief of hot flushes and genital atrophy and for prevention of postmenopausal osteoporosis.

It was surprisingly found that the Selective Progesterone Receptor Modulators (SPRM) of present invention are beside being potent Progesterone Receptor antagonist able to successfully treat and/or provide prophylaxis against sexual hormone dependent diseases and gynaecological diseases, preferably Endometriosis or Uterine Fibroids characterized in that a reduced risk of various physiological changes including vulvar and vaginal atrophy causing vaginal dryness, pruritus and dyspareunia, and vasomotor instability manifested as hot flushes and loss of bone mineral density is observed which is typically seen with Selective Progesterone Receptor Modulators (SPRM) resulting from the decline of endogenous estradiol concentration during treatment

DESCRIPTION OF THE INVENTION

Figure 1:
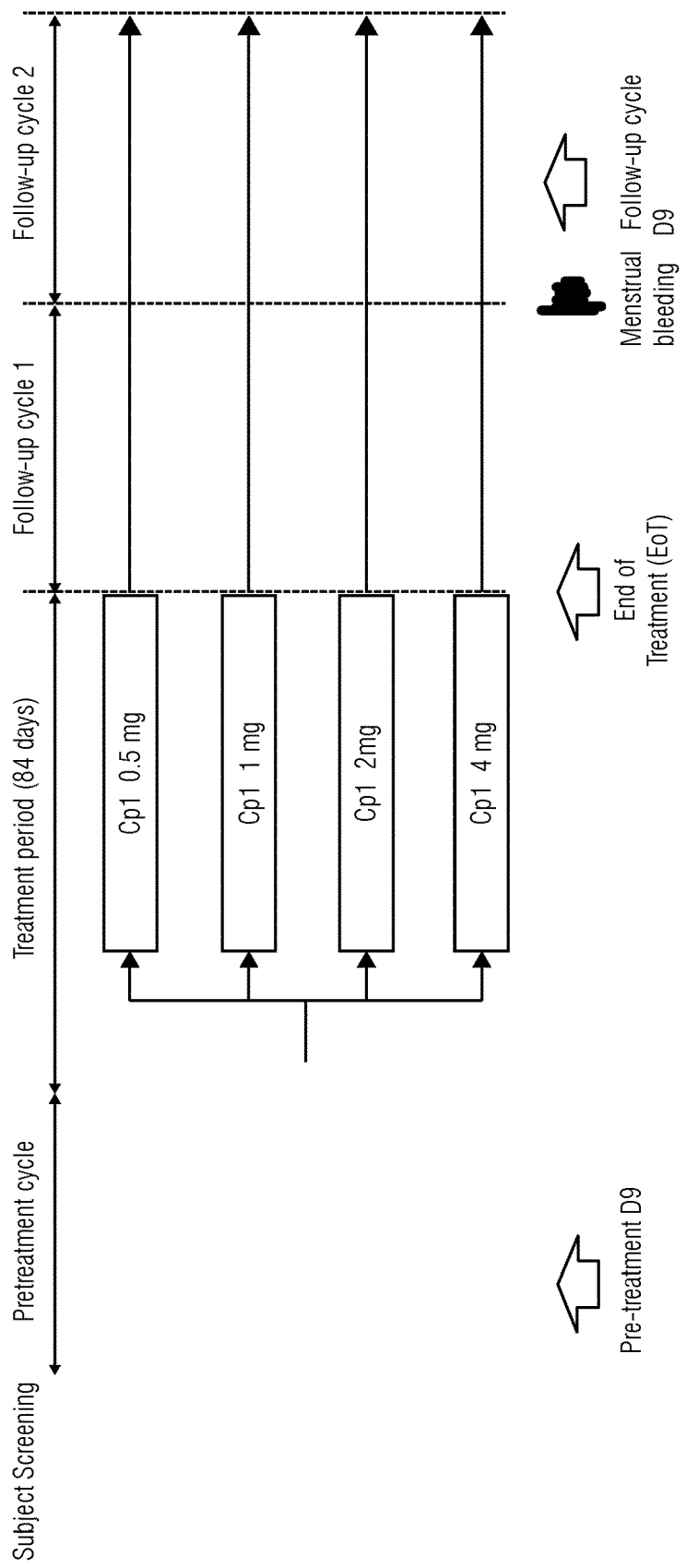
FIG. 1 depicts accessing estradiol (E2) serum concentration for each subject at different days during a study.

First Aspect:

The present invention is directed to Selective Progesterone Receptor Modulators (SPRM) namely (11β,17β)-17-Hydroxy-11-[4-(methylsulphonyl)phenyl]-17-(pentafluoroethyl)estra-4,9-dien-3-one (Compound 1) of formula (I)

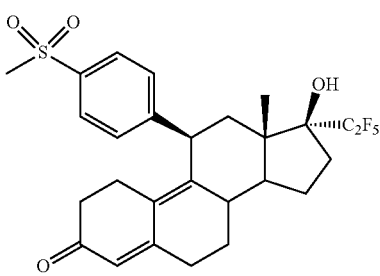

or a stereoisomer, a tautomer, a hydrate, a solvate, or a pharmaceutically acceptable salt thereof, or a mixture of same wherein said Compound 1 as defined above is administered to women in need of treatment as detailed below in a daily dosage of 1 mg to 5 mg during a treatment period of four (4) weeks to one (1) year:
for use in the treatment and/or prophylaxis of a sexual hormone dependent disease and gynaecological disease, preferably, the disease is selected from Endometriosis, Uterine Fibroids (UF) and associated symptoms thereof;
characterized in that Compound 1 as defined above is reducing the risk of estrogen-depletion associated with physiological changes selected from vulvar and vaginal atrophy causing vaginal dryness, pruritus and dyspareunia, and vasomotor instability manifested as hot flushes and loss of bone mineral density wherein at least one of these physiological changes applies.

In other words, the invention is directed to a method for reducing the risk of estrogen-depletion associated with physiological changes selected from vulvar and vaginal atrophy causing vaginal dryness, pruritus and dyspareunia, and vasomotor instability manifested as hot flushes and loss of bone mineral density wherein at least one of these physiological changes applies, comprising the step of administering Selective Progesterone Receptor Modulators (SPRM) namely (11β,17β)-17-Hydroxy-11-[4-(methylsulphonyl)phenyl]-17-(pentafluoroethyl)estra-4,9-dien-3-one (Compound 1) of formula (I)

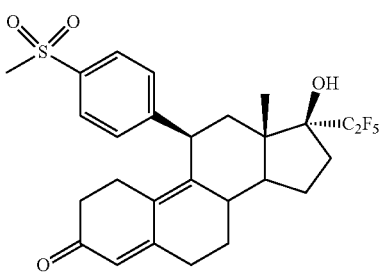

or a stereoisomer, a tautomer, a hydrate, a solvate, or a pharmaceutically acceptable salt thereof, or a mixture of same to women in need of treatment and/or prophylaxis of a sexual hormone dependent disease and gynaecological disease, preferably, the disease is selected from Endometriosis, Uterine Fibroids (UF) and associated symptoms thereof; in a daily dosage of 1 mg to 5 mg during a treatment period of four (4) weeks to one (1) year.

The woman in need of treatment is defined as female human that is suffering of Endometriosis, Uterine Fibroids (UF) and/or associated symptoms thereof and responding in general to known Selective Progesterone Receptor Modulators (SPRM) treatment by a decrease of their circulating endogenous estradiol concentrations in blood plasma and/or physiological changes as mentioned above are observed. The circulating endogenous estradiol level characteristically decrease preferably to a concentration below 40 pg/mL in blood plasma. The Selective Progesterone Receptor Modulators (SPRM) thereof for which such observations are made is never Compound 1.

Second Aspect:

The present invention is directed to Selective Progesterone Receptor Modulators (SPRM) namely (11β,17β)-17-Hydroxy-11-[4-(methylsulphonyl)phenyl]-17-(pentafluoroethyl)estra-4,9-dien-3-one (Compound 1) of formula (I)

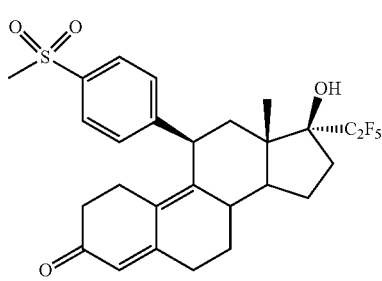

or a stereoisomer, a tautomer, a hydrate, a solvate, or a pharmaceutically acceptable salt thereof, or a mixture of same wherein said Compound 1 as defined above is administered to women in need of treatment as detailed below in a daily dosage of 1 mg to 5 mg during a treatment period of four (4) weeks to one (1) year;
for use in the treatment and/or prophylaxis of a sexual hormone dependent disease and gynaecological disease, preferably, the disease is selected from Endometriosis, Uterine Fibroids (UF) and associated symptoms thereof;
characterized in that the circulating endogenous estrogen concentrations in women are maintained to a level within the range of 40 pg/mL to 85 pg/mL during the treatment period.

In other words, the invention is directed to a method for maintaining the circulating endogenous estrogen concentrations to a level within the range of 40 pg/mL to 85 pg/mL during the treatment period comprising the step of administering Selective Progesterone Receptor Modulators (SPRM) namely (11β,17β)-17-Hydroxy-11-[4-(methylsulphonyl)phenyl]-17-(pentafluoroethyl)estra-4,9-dien-3-one (Compound 1) of formula (I)

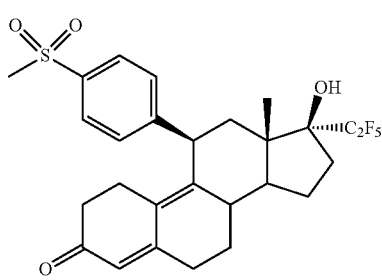

or a stereoisomer, a tautomer, a hydrate, a solvate, or a pharmaceutically acceptable salt thereof, or a mixture of same in a daily dosage of 1 mg to 5 mg during a treatment period of four (4) weeks to one (1) year; to women in need of treatment and/or prophylaxis of a sexual hormone dependent disease and gynaecological disease, preferably, the disease is selected from Endometriosis, Uterine Fibroids (UF) and associated symptoms thereof.

The woman in need of treatment is defined as female human that is suffering of Endometriosis, Uterine Fibroids (UF) and/or associated symptoms thereof and responding in general to known Selective Progesterone Receptor Modulators (SPRM) treatment by a decrease of their circulating endogenous estradiol concentrations in blood plasma and/or physiological changes as mentioned above are observed. The circulating endogenous estradiol level characteristically decrease preferably to a concentration below 40 pg/mL in blood plasma. The Selective Progesterone Receptor Modulators (SPRM) thereof for which such observations are made is never Compound 1.

Preferably, the woman in need of treatment is suffering of Endometriosis and/or Uterine Fibroids (UF).

Third Aspect:

The present invention is directed to Selective Progesterone Receptor Modulators (SPRM) namely (11β,17β)-17-Hydroxy-11-[4-(methylsulphonyl)phenyl]-17-(pentafluoroethyl)estra-4,9-dien-3-one (Compound 1) of formula (I)

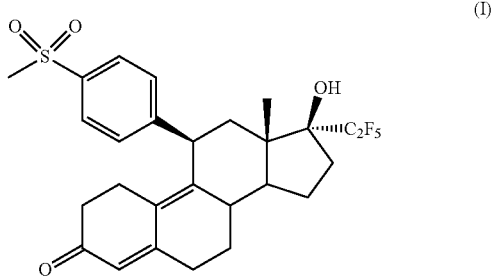

(I)

or a stereoisomer, a tautomer, a hydrate, a solvate, or a pharmaceutically acceptable salt thereof, or a mixture of same wherein the Compound 1 as defined above is administered to women in need of treatment as detailed below in a daily dosage of 1 mg to 5 mg during a treatment period of four (4) weeks to one (1) year;
for use in the treatment and/or prophylaxis of a sexual hormone dependent disease, preferably, the disease is selected from Endometriosis, Uterine Fibroids (UF) and associated symptoms thereof;
Characterized in that
women in need of treatment are diagnostized as developing estrogen-depletion associated with physiological changes and/or are potentially at risk of estrogen-depletion associated with physiological changes selected from vulvar and vaginal atrophy causing vaginal dryness, pruritus and dyspareunia, and vasomotor instability manifested as hot flushes and loss of bone mineral density when treated with Selective Progesterone Receptor Modulators (SPRM) such as but not limited to Ulipristal acetate (UPA) or Gonadotrophin-Releasing Hormone (GnRH) analogues such as but not limited to Leuprolide and Elagolix.

Preferably, with proviso that SPRM is not defined as Compound 1.

In other words, the invention is directed to a method of treatment and/or prophylaxis of a sexual hormone dependent disease and gynaecological disease, preferably, the disease is selected from Endometriosis, Uterine Fibroids (UF) and associated symptoms thereof; wherein women in need of treatment are diagnostized as developing estrogen-depletion associated with physiological changes and/or are potentially at risk of estrogen-depletion associated with physiological changes selected from vulvar and vaginal atrophy causing vaginal dryness, pruritus and dyspareunia, and vasomotor instability manifested as hot flushes and loss of bone mineral density when treated with Selective Progesterone Receptor Modulators (SPRM) such as but not limited to Ulipristal acetate (UPA) or Gonadotrophin-Releasing Hormone (GnRH) analogues such as but not limited to Leuprolide and Elagolix comprising the step of diagnosing women at risk and/or identifying women potentially at risk and then administering Selective Progesterone Receptor Modulators (SPRM) namely (11β,17β)-17-Hydroxy-11-[4-(methylsulphonyl)phenyl]-17-(pentafluoroethyl)estra-4,9-dien-3-one (Compound 1) of formula (I)

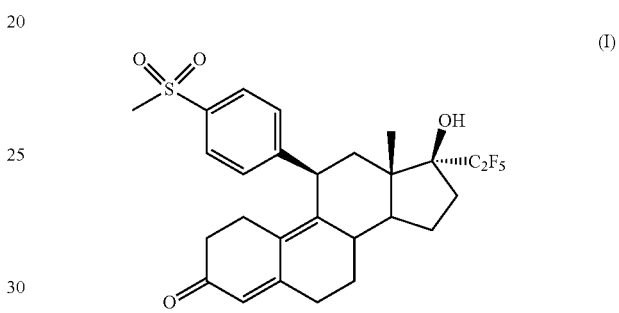

(I)

or a stereoisomer, a tautomer, a hydrate, a solvate, or a pharmaceutically acceptable salt thereof, or a mixture of same in a daily dosage of 1 mg to 5 mg during a treatment period of four (4) weeks to one (1) year.

The woman in need of treatment is defined as female human that is suffering of Endometriosis, Uterine Fibroids (UF) and/or associated symptoms thereof and responding in general to known Selective Progesterone Receptor Modulators (SPRM) treatment by a decrease of their circulating endogenous estradiol concentrations in blood plasma and/or physiological changes as mentioned above are observed. The circulating endogenous estradiol level characteristically decrease preferably to a concentration below 40 pg/mL in blood plasma. The Selective Progesterone Receptor Modulators (SPRM) thereof for which such observations are made is never Compound 1.

Preferably, the woman in need of treatment is suffering of Endometriosis and/or Uterine Fibroids (UF).

Embodiments and Preferred Features Applicable to the First, Second and Third Aspects Respectively as Described Above In one embodiment the daily dosage is in a range from 2 to 4 mg of Compound 1 as defined above. Preferably, the daily dosage is of about 2 or 4 mg of Compound 1 as defined above. More preferably, the daily dosage is of about 2 mg of Compound 1 as defined above. The dosage is defined to be applied to an adult patient.

In one embodiment, the treatment period is defined as period where Compound 1 is continuously administered during a period of four (4) weeks to one (1) year or optionally the treatment period is followed by a break period where administration of Compound 1 is discontinued until one (1) or two (2) menstrual bleeding episodes occur and treatment period and break period as defined above are repeated at least one (1) time. Preferably, the treatment period is defined as period where Compound 1 is continuously administered during at least 6 months to one (1) year. More preferably, the treatment period is defined as period where Compound 1 is continuously administered during about 6 months.

In one embodiment, the treatment period is defined as period where Compound 1 is continuously administered during a period of four (4) weeks to one (1) year and additionally the treatment period is followed by a break period where administration of Compound 1 is discontinued until one (1) or two (2) menstrual bleeding episodes occur and treatment period and break period as defined above are repeated at least one (1) time.

Preferably, the treatment period is defined as a period where Compound 1 is continuously administered during a period of twelve (12) weeks followed by a break period where administration of Compound 1 is discontinued until one (1) menstrual bleeding episode occur and treatment period of twelve (12) weeks is restarted.

Preferably, the treatment period is defined as a period where Compound 1 is continuously administered during a period of twenty-four (24) weeks followed by a break period where administration of Compound 1 is discontinued until one (1) or two (2) menstrual bleeding episodes occur and treatment period of twenty-four (24) weeks is restarted. Preferably, break period corresponds to a period where administration of Compound 1 is discontinued until two (2) menstrual bleeding episodes occur.

Preferably, treatment period and break period are repeated one (1) to five (5) times, more preferably one (1) or two (2) times or one (1) time.

In a further embodiment, the treatment period is defined as a period where Compound 1 is continuously administered during a period of twelve (12) weeks up to twenty-four (24) weeks.

Preferably, the treatment period is defined as a period where Compound 1 is continuously administered during a period of twelve (12) weeks up to fifteen (15) weeks.

Preferably, the treatment period is defined as a period where Compound 1 is continuously administered during a period of sixteen (16) weeks up to twenty four (24) weeks.

In one embodiment, the treatment and/or prophylaxis is to apply to women in need of treatment suffering from sexual hormone dependent diseases selected from Endometriosis, Uterine Fibroids (UF) and associated symptoms thereof.

Preferably, the treatment and/or prophylaxis are to apply to women in need of treatment suffering from Endometriosis and associated symptoms thereof.

Endometriosis associated symptoms are defined as, but not limited to, pelvic pain and Dysmenorrhoea (i.e. excessive pain during menstruation), Dyspareunia (i.e. painful sexual intercourse) or infertility.

Preferably, Endometriosis associated symptoms are defined as pelvic pain and Dysmenorrhoea (i.e. excessive pain during menstruation) or Dyspareunia (i.e. painful sexual intercourse) Preferably, the treatment and/or prophylaxis are to apply to women in need of treatment suffering from Uterine Fibroids (UF) and associated symptoms thereof.

Uterine Fibroids (UF) associated symptoms are defined as, but not limited to, pelvic pain, infertility, Heavy Menstrual Bleeding (HMB) and bleeding or spotting between menstruation periods.

Preferably, Uterine Fibroids (UF) associated symptoms are defined as pelvic pain, Heavy Menstrual Bleeding (HMB) and bleeding or spotting between menstruation periods. More preferably, Uterine Fibroids (UF) associated symptoms are defined as Heavy Menstrual Bleeding (HMB) and bleeding or spotting between menstruation periods. Even more preferably, Uterine Fibroids (UF) associated symptoms are defined as, Heavy Menstrual Bleeding (HMB).

Heavy menstrual bleeding (HMB) occurs as a symptom of Uterine Fibroids (UF) or Endometriosis. Heavy menstrual bleeding is considered to be when 60 mL or more blood is lost in each menstrual cycle.

In one embodiment, the estrogen-depletion associated with physiological changes are selected from hot flushes and loss of bone mineral density. Preferably, the estrogen-depletion associated with physiological change is hot flushes where the hot flushes appear in no more that 25% of the treated women. Preferably, the hot flushes occur in a range of 5% to 25% of the treated women. More preferably, the hot flushes occur in a range of 5% to 10%, 8% to 14%, 8% to 10% or 10% to 20% in the treated women. Even more preferably, the hot flushes occur in about 10% in the treated women with a standard variation of no more than +/−2%.

In one embodiment, the hot flushes are distinguished into mild, moderate or severe hot flush. Preferably, the hot flushes are mild- or moderate-hot flush. More preferably, the hot flushes are mild- or moderate-hot flush and appear in no more that 25% of the treated women. Preferably, the hot flushes are mild- or moderate-hot flush and the hot flushes appear in a range of 5% to 25% of the treated women. More preferably, the hot flushes are mild- or moderate-hot flush and the hot flushes appear in a range of 5% to 10%, 8% to 14%, 8% to 10% or 10% to 20% in the treated women. Even more preferably, the hot flushes are mild- or moderate-hot flush and the hot flushes occur in about 10% in the treated women with a standard variation of no more than +/−2%.

In one embodiment, the circulating endogenous estrogen in women is 17β-estradiol.

In one embodiment, the circulating endogenous estrogen concentrations in women, in particular Estradiol (E2) is maintained to a level within the range of 40 pg/mL to 85 pg/mL during the treatment period. Preferably, the circulating endogenous estrogen concentrations in women is maintained to a level within the range of 50 pg/mL to 85 pg/mL during the treatment period. More preferably, the circulating endogenous estrogen concentrations in women is maintained to a level within the range of 70 pg/mL to 85 pg/mL or the range of 70 pg/mL to 80 pg/mL or the range of 40 pg/mL to 60 pg/mL, the range of 40 pg/mL to 70 pg/mL or the range of 40 pg/mL to 80 pg/mL during the treatment period.

In a further embodiment, the circulating endogenous estrogen concentrations in treated women, in particular Estradiol (E2), is never lower than 40 pg/mL during the treatment period. Preferably, the circulating endogenous estrogen concentrations in particular Estradiol (E2), in treated women is never lower than 50 pg/mL during the treatment period. More preferably, the circulating endogenous estrogen concentrations in particular Estradiol (E2), in women is never lower than 70 pg/mL during the treatment period.

In a further embodiment, the circulating endogenous estrogen concentrations in treated women, in particular Estradiol (E2), is decreasing during the treatment period compared to the circulating endogenous estrogen concentrations baseline at treatment start but never lower than 40 pg/mL and this reduction is reversible after the end of the treatment period.

In a further embodiment, the circulating endogenous estrogen concentrations in women, in particular Estradiol (E2), is maintained to a level within the range of 40 pg/mL to 85 pg/mL during the treatment period in at least 70% of the women, preferably in a range of 80% to 90% of the women.

Definitions

The terms as mentioned in the present text have the following meanings:

Effective suppression of the endocrine ovarian function means that estrogen serum concentrations (notably 17β-estradiol-levels) and consequently endogenous progesterone serum concentrations will be suppressed to such a level that virtually no growth of endometrial tissue will occur. When the ovaries are sufficiently suppressed, this will normally induce amenorrhoea.

A bleeding episode is at least one day of menstrual bleeding.

The treatment period means the period where the invention Compound 1 is administered to the women in need of treatment.

Hot flushes refer to sudden feelings of heat or burning which starts in the head and neck area and then passes, often in waves, over the entire body. Immediately thereafter objective signs of body heat dissipation by sweating and peripheral vasodilation are usually observed (Freedman; Physiology of hot flashes; Am. J. Human Biology, Vol 13 pp 453-464, 2001). Hot flushes is a vasomotor deficiency symptom.

The invention range of 40 pg/mL to 85 pg/mL of circulating endogenous estradiol concentrations refers to Median or Mean values.

For the purpose of clarity, estradiol and estrogen are used with similar meaning.

Circulating endogenous estrogen refers to the naturally estrogen hormone circulating in blood. Naturally occurring forms of estrogen in women are estrone (E1), estradiol (E2), and estriol (E3). Another type of estrogen called estetrol (E4) is produced only during pregnancy.

Women in need of treatment are female humans (subject) suffering from sexual hormone dependent diseases and gynaecological diseases selected from Endometriosis, Uterine Fibroids (UF) and associated symptoms thereof.

Most common symptoms related to Uterine Fibroids (UF) are pelvic pain, infertility, Heavy Menstrual Bleeding (HMB) and bleeding or spotting between menstruation periods. Preferably, treated symptom is Heavy Menstrual Bleeding (HMB).

Most common symptoms related to Endometriosis are pelvic pain and Dysmenorrhoea (i.e. excessive pain during menstruation), Dyspareunia (i.e. painful sexual intercourse) and infertility. Preferably, treated symptom is Dysmenorrhoea.

The reduced circulating endogenous estrogen refers to value that did not reach postmenopausal levels i.e. lower than 27 pg/mL of estradiol (E2). Mild hot flush refers to flashes or flushes that are barely noticeable and don't interfere with daily routine, normally lasting less than five minutes.

Moderate hot flush refers to flashes or flushes that are more intense and noticeable, often including a bothersome feeling of heat in the upper body and irregular heartbeat. Severe hot flush refers to flashes or flushes that force women to seek immediate relief. They consist of profuse sweating, cold chills, and dizziness, among other symptoms.

The wording "during the treatment period" means here until the end of the treatment period corresponding to the last time Compound 1 is administered in women suffering from sexual hormone dependent diseases and gynaecological diseases selected from Endometriosis, Uterine Fibroids (UF) and associated symptoms thereof.

The term "comprising" when used in the specification includes "consisting of".

The term depletion means a visible and measurable reduction.

The twelve (12) weeks is to be equivalent to about 3 months.

The twenty-four (24) weeks is to be equivalent to about 6 months.

The wording "to treat and/or prophylaxis diseases" means "to treat said diseases and/or provide prophylaxis against said diseases".

The wording "potentially at risk" means that in view of women disease historic, weight, ethny and/or other parameters women can be classified as reacting negatively to a certain treatment.

The wording "break period" means that administration of Compound 1 is discontinued until at least one menstrual bleeding occur. Spotting shall not be compted as menstrual bleeding. Preferably, the menstrual bleeding shall occur one (1) to five (5) times.

If within the present text any item is referred to as "as mentioned herein", it means that it may be mentioned anywhere in the present text.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

The present invention includes all possible tautomers of the compounds of the present invention as single tautomers, or as any mixture of said tautomers, in any ratio.

The present invention also covers useful forms of the compounds of the present invention, such as metabolites, hydrates, solvates, prodrugs, salts, in particular pharmaceutically acceptable salts, and/or co-precipitates.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

The present invention includes all possible salts of the compounds of the present invention as single salts, or as any mixture of said salts, in any ratio.

Compounds of present invention are administered in the form of unit dose e.g tablet.

The invention is directed to gynaecological diseases like adenomyosis, dysmenorrhoea and functional menorrhagia and metrorrhagia, Endometriosis, Uterine Fibroids (UF) and associated symptoms thereof. Said gynaecological disorders are all estrogen sensitive. The available pharmaceutical treatments, however, suffer from the major drawbacks as mentioned above, i.e. they have to be discontinued once the side-effects become more serious than the symptoms to be treated and restoring of life quality is not achieved.

EXPERIMENTAL SECTION

Experimental Section—General Part

All reagents, for which the synthesis is not described in the experimental part, are either commercially available, or are known compounds or may be formed from known compounds by known methods by a person skilled in the art.

Experimental Section—Chemistry

Example 1: Synthesis of (11β,17β)-17-Hydroxy-11-[4-(methylsulphonyl)phenyl]-17-(pentafluoroethyl)estra-4,9-dien-3-one (Compound 1)

The production of (11β,17β)-17-hydroxy-11-[4-(methylsulfonyl)phenyl]-17-(pentafluoroethyl)estra-4,9-dien-3-one (CAS-No. 1262108-14-4; Compound 1) is described in WO2011/009531 and DE 102009034362 and can be carried out by analogy with the instructions contained therein.

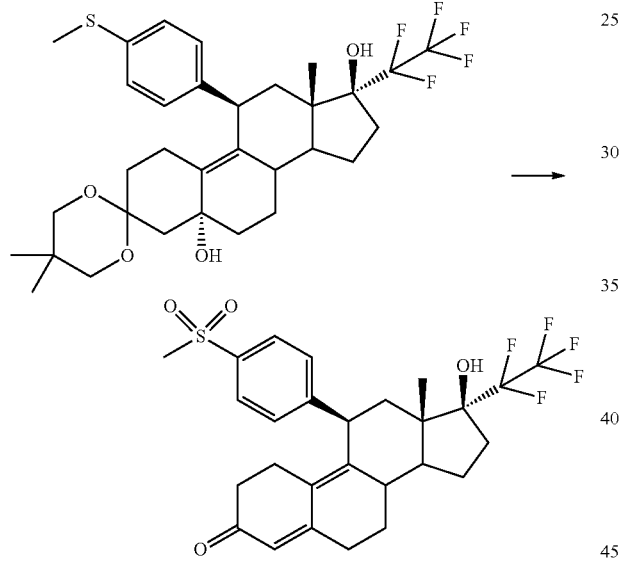

5 g of the compound described above was dissolved in a mixture of 140 mL THF and 140 mL methanol. A solution of 20 g Oxone® in 94 mL water was slowly added dropwise at 0° C. Then it was stirred for a further 3.5 hours at 0° C. Then a mixture of water and dichloromethane was added to the reaction mixture. The phases were separated and the aqueous phase was extracted several times with dichloromethane. The combined organic phases were washed with saturated aqueous sodium chloride solution, dried over sodium sulphate and concentrated under vacuum. The raw product was purified by silica gel chromatography. This gave 3.8 g of the title compound. 1H-NMR (300 MHz, CDCl3): δ=7.86 d (2H); 7.40 d (2H); 5.81 sbr (1H); 4.50 dbr (1H); 3.07 s (3H): 0.51 s (3H).

Experimental Section—Biological Assays

Example 2: Circulating Endogenous Estrogen Concentrations in Healthy Women of Reproductive Age Receiving Compound 1 (Cp1)

Study protocol (N° 15818): A randomized, double-blind, parallel-group, multi-center study to investigate the pharmacodynamics, pharmacokinetics and safety after daily oral administration of 4 different doses of Compound 1 in healthy women of reproductive age Study Description:
Test drug: Compound 1 (Cp1)
Doses: 0.5 mg, 1 mg, 2 mg, or 4 mg once daily
Route of administration: Oral
Duration of treatment: 1×12 weeks (84 days)
Main criteria for inclusion of Subjects:
Healthy female subjects
   Age: 18-40 years
   Smoking ≤10 cigarettes/day
   Body mass index ≥18 and ≤32 kg/m$^2$
   Signed informed consent prior to study participation
   No contraindication for intake of Compound 1
   Ovulation in pre-treatment cycle
   Use of non-hormonal contraception during the study.
Number of Subjects: see Table 1 for the number of subjects per Dosage
Measurement of primary variable Estradiol:
The estradiol (E2) serum concentration was assessed for each subject at the following Visit Days of the study, see FIG. 1
   Pre-treatment Day 9 (D9) corresponds to the period before start of Compound 1 uptake; the pre-treatment cycle starts on the first day of the subject waking up with menstrual bleeding with intensity more than spotting after screening examinations have shown that the subject is eligible for further participation. The pre-treatment period ends by the starting of next menstrual bleeding;
   Treatment Day (D84) corresponds to last intake of Compound 1. The treatment phase started with the first and ended with the last intake of the study drug. The subjects have to start the intake of Compound 1 during the first week of the menstrual cycle after the pre-treatment cycle until the last Treatment Day (D84).
   The follow-up cycle 1 started on the first day without study drug intake and will end in case of start of menstrual bleeding (i.e. when the subject is waking up with menstrual bleeding with intensity more than spotting). The first day of menstrual bleeding will define the start of follow-up cycle 2. Follow-up cycle 2 ended when the subjects report the next menstrual bleeding (i.e. first day of waking up with menstrual bleeding with intensity more than spotting).

During pre-treatment, end of treatment and at Follow-up Cycle 2, Estradiol (E2) serum concentrations are measured.

Treatment Period:

Eligible subjects were randomized to one of the treatment groups (0.5 mg, 1 mg, 2 mg, or 4 mg Compound 1). The treatment period consisted of 12 weeks (84 days) of daily tablet intake.

Results:

Table 1 shows the estradiol (E2) concentrations in serum of the study subjects at different Visit days. A slight decrease of estradiol (E2) concentrations is observed during treatment with Compound 1. This observation is completely reversible after end of treatment as seen by comparison of E2 concentrations at pre-treatment and follow-up Cycle 2.

At the last day (Day 84) the Median Estradiol (E2) value is about 80 pg/mL at the dose groups 0.5, 1 and 2 mg and about 50 pg/mL at the 4 mg dose group.

Example 3: Hot Flush Event in Study Subject Treated with Compound 1 (Cp1)

See full study description in Example 2.

Hot flush event were reported and monitored during treatment period.

Results:

Hot flush was reported in 11 subjects from the total study subjects with increasing frequency of hot flush in the higher dose groups, see Table 2. No severe hot flushes were reported. Subjects reported only mild to moderate hot flushes.

TABLE 1

Study 15818 Estradiol concentrations in serum

| Dose Cp1 | Visit Day | Number of Subjects (N) | Mean pg/mL | SD pg/mL | Min pg/mL | Median pg/mL | Max pg/mL |
|---|---|---|---|---|---|---|---|
| 0.5 mg | Pre-treatment D 9 | 16 | 138 | 117.9 | 14 | 104.5 | 381 |
|  | Treatment D 84 | 17 | 135.6 | 122 | 23 | 82 | 423 |
|  | Follow-up cycle2 D 9 | 17 | 116.1 | 81.8 | 17 | 79.9 | 262 |
| 1 mg | Pre-treatment D 9 | 17 | 143.3 | 95 | 39 | 92.3 | 311 |
|  | Treatment D 84 | 17 | 119.4 | 76.5 | 42 | 81.5 | 276 |
|  | Follow-up cycle2 D 9 | 17 | 143.8 | 84.7 | 39 | 119.2 | 305 |
| 2 mg | Pre-treatment D 9 | 16 | 113.5 | 72.8 | 33 | 82.2 | 308 |
|  | Treatment D 84 | 15 | 91.2 | 73.1 | 34 | 78.5 | 330 |
|  | Follow-up cycle2 D 9 | 16 | 123.9 | 102.1 | 33 | 80.9 | 395 |
| 4 mg | Pre-treatment D 9 | 16 | 126.4 | 47.9 | 44 | 122.9 | 200 |
|  | Treatment D 84 | 16 | 53.9 | 13.6 | 39 | 50.5 | 81 |
|  | Follow-up cycle2 D 9 | 16 | 109.9 | 62.3 | 41 | 88.7 | 279 |

SD: Standard Deviation
Cp1: Compound 1

TABLE 2

Hot flush events

| Dose Cp1 | Number of subjects (N) | Events (%) |
|---|---|---|
| 0.5 mg | 1 | 5.6 |
| 1.0 mg | 2 | 11.1 |
| 2.0 mg, | 3 | 17.6 |
| 4.0 mg | 5 | 29.4 |

Cp1: Compound 1

Example 4: Clinical Study in Women Diagnosed with Uterine Fibroids During a 1×12 Weeks/84 Days Treatment with Compound 1

Study protocol (N° 15788):
Test drug: Compound 1
Doses: 0.5 mg, 1 mg, 2 mg, or 4 mg once daily
Route of administration: Oral
Duration of treatment: 1×12 weeks (84 days)
Reference drug: Placebo
Duration of treatment: 1×12 weeks (84 days)
Diagnosis and main criteria for inclusion of Subjects:
Women, 18 to 50 years old, with uterine fibroids documented by transvaginal or abdominal ultrasound at screening with at least 1 uterine fibroid with largest diameter 3 cm and Heavy Menstrual Bleeding (HMB) 80 mL were eligible for enrolment in the study.
Number of Women:
  Randomized: 309
  Started treatment: 300
  Completed treatment: 286
  Completed follow-up: 243

Screening Period:

Following screening visit 1 (Visit 1), there was a screening period of up to 90 days to arrange for complete results of all baseline assessments. During the screening period, subjects were to demonstrate eligibility including presence of at least 1 uterine fibroid of maximum 3 cm diameter and a diagnosis of HMB, defined as menstrual blood loss 80 mL assessed by menstrual pictogram (MP) during the bleeding episode following the screening visit 1 (Visit 1). Every effort was made to keep the duration of the screening period to a minimum.

Treatment Period:

Eligible subjects were equally randomized to one of the treatment groups (Placebo, 0.5 mg, 1 mg, 2 mg, or 4 mg Compound 1). Treatment was started during the first week of the menstrual cycle following randomization. The treatment period consisted of 12 weeks (84 days) of daily tablet intake.

Figure 2:
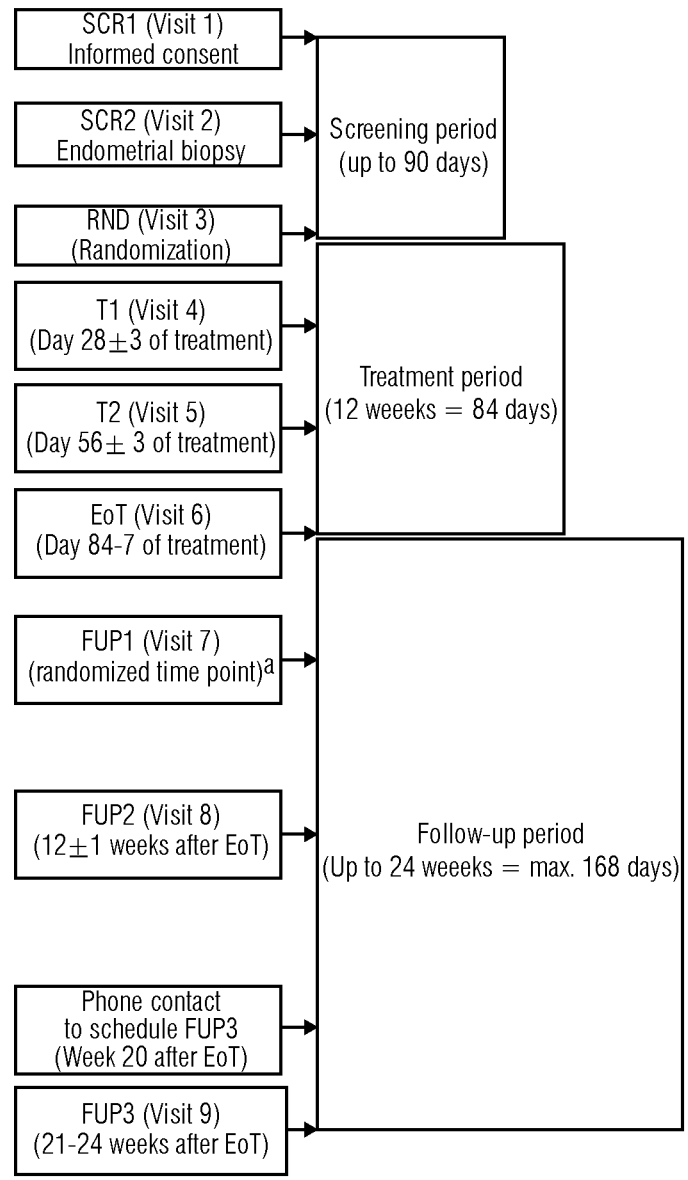
FIG. 2 depicts a description of a clinical study in women diagnosed with uterine fibroids during a 1×12 weeks/84 days treatment with Compound 1.

Full description of the study in FIG. 2.

FIG. 2: Study design overview
EoT: End of Treatment visit
FUP: Follow-up visit 1
RND: Randomization visit
SCR1, 2: Screening visit 1, 2
T1, 2, 3, 4, 5, 6: Treatment visit 1, 2, 3, 4, 5, 6
B: Break period, duration depending on group allocation
TP1, 2: Treatment period 1, 2
In this study, estradiol levels were measured
At the End of Treatment (EoT) visit and
Randomization visit 3.

Results:

Overall, estradiol levels under treatment were moderately suppressed compared to baseline. A trend of decreasing unbound estradiol concentrations with increasing Compound 1 exposure was noted. While the Median value at End of Treatment (EoT) was the same for the 1 mg and 2 mg dose (50 pg/mL), in the 4 mg it was lower (39 pg/mL), see Table 3. After the EoT, the Mean estradiol values returned to baseline levels for all Doses, data not shown.

Thus, Estradiol levels under treatment were moderately suppressed compared to baseline, but individual values remained mostly within the physiological follicular phase range. Overall, no safety concerns were identified from the data analysed.

TABLE 3

Study 15788 Estradiol concentrations in serum

| Cp1 Dose | Visit Day | Number of Subjects (N) | Mean pg/mL | SD pg/mL | Min pg/mL | Median pg/mL | Max pg/mL |
|---|---|---|---|---|---|---|---|
| Placebo | Randomization | 57 | 110.1 | 92.86 | 8.4 | 90.8 | 504.4 |
| Placebo | End of Treatment | 53 | 127.58 | 105.44 | 10 | 110.3 | 564.8 |
| 0.5 mg | Randomization | 58 | 115.78 | 69.16 | 7.1 | 100.2 | 318.6 |
| 0.5 mg | End of Treatment | 57 | 97.3 | 90.81 | 8.3 | 56.9 | 357.5 |
| 1 mg | Randomization | 60 | 120.72 | 90.83 | 21.5 | 103.65 | 490.2 |
| 1 mg | End of Treatment | 61 | 72.85 | 72.43 | 11.8 | 50.1 | 384.9 |
| 2 mg | Randomization | 60 | 111.25 | 73.29 | 6.7 | 96.6 | 407.8 |
| 2 mg | End of Treatment | 60 | 76.23 | 79.72 | 10.5 | 49.95 | 433.9 |
| 4 mg | Randomization | 60 | 117.05 | 81.77 | 6.8 | 101.7 | 347.6 |
| 4 mg | End of Treatment | 54 | 56.51 | 48.52 | 9.5 | 38.7 | 255.3 |

SD: Standard Deviation
Cp1: Compound 1

Example 5: Hot Flush Events in Study Subject Treated with Compound 1 (Cp1)

See full study description in Example 4.
Hot flush events were reported and monitored during treatment.
Results:
A single severe hot flush event occurred when subject treated with 0.5 mg of Compound 1. Overall, no more than 14% of the subjects show mild to moderate hot flushes, see Table 4.

TABLE 4

Hot flush events

| | Cp1 Dose Group | | | | | |
|---|---|---|---|---|---|---|
| | 4 mg | 2 mg | 1 mg | 0.5 mg | Placebo | Total |
| Number of Subjects (N)/Intensity | N = 60 (100%) | N = 61 (100%) | N = 61 (100%) | N = 60 (100%) | N = 58 (100%) | N = 300 (100%) |
| MILD | 5 (8.3%) | 4 (6.6%) | 3 (4.9%) | 5 (8.3%) | 3 (5.2%) | 20 (6.7%) |
| MODERATE | 3 (5.0%) | 1 (1.6%) | 2 (3.3%) | 0 | 1 (1.7%) | 7 (2.3%) |
| SEVERE | 0 | 0 | 0 | 1 (1.7%) | 0 | 1 (0.3%) |
| Total | 8 (13.3%) | 5 (8.2%) | 5 (8.2%) | 6 (0.0%) | 4 (6.9%) | 28 (9.3%) |

Cp1: Compound 1

Example 6: Clinical Study in Women Diagnosed with Uterine Fibroids During a 1×24 Weeks Treatment with Compound 1

Study protocol (N° 17541/A1):
Test drug: Compound 1
Doses: 2 mg once daily
Route of administration: Oral
Duration of treatment: 1×24 weeks
Diagnosis and main criteria for inclusion of Subjects:
Women, 18 to 50 years old, with uterine fibroids documented by transvaginal or abdominal ultrasound at screening with at least 1 uterine fibroid with largest diameter >3 cm and Heavy Menstrual Bleeding (HMB)>80 mL were eligible for enrolment in the study.

Screening Period:
Following screening visit 1 (Visit 1), there was a screening period of up to 90 days to arrange for complete results of all baseline assessments. During the screening period, subjects were to demonstrate eligibility including presence of at least 1 uterine fibroid of maximum 3 cm diameter and a diagnosis of HMB, defined as menstrual blood loss 80 mL assessed by menstrual pictogram (MP) during the bleeding episode following the screening visit 1 (Visit 1). Every effort was made to keep the duration of the screening period to a minimum.

Treatment Period:
Eligible subjects were equally randomized to treatment 2 mg of Compound 1. Treatment was started during the first week of the menstrual cycle following randomization. The treatment period consisted of 24 weeks of daily tablet intake.

Figure 3:
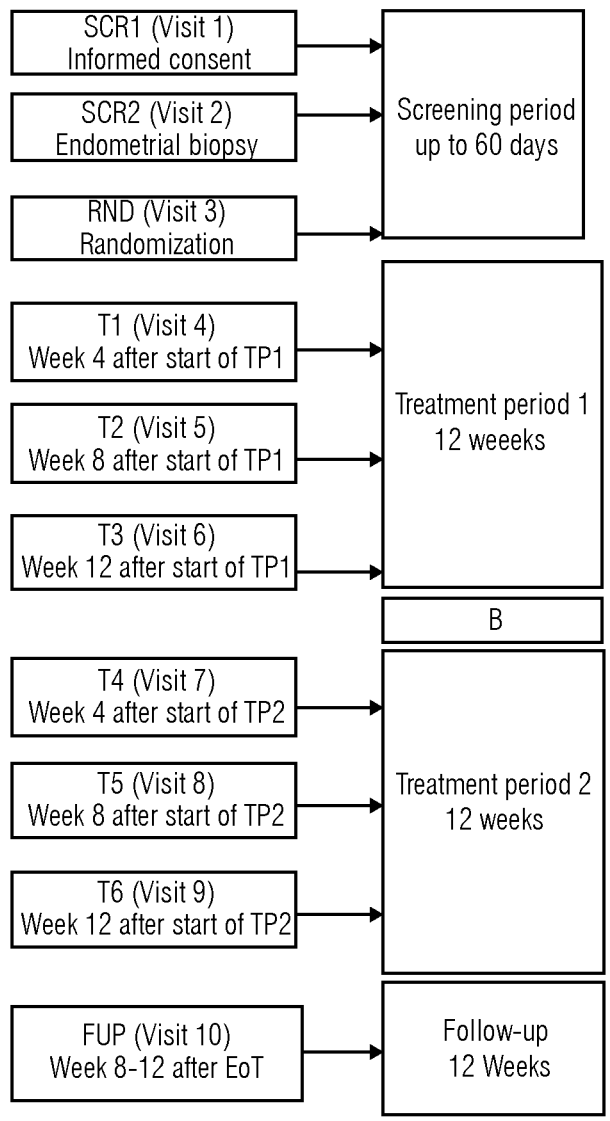
FIG. 3 depicts clinical study in women diagnosed with uterine fibroids during a 1×24 weeks treatment with Compound 1.

Full description of the study in FIG. 3.
FIG. 3: Study design overview
  EoT: End of Treatment visit
  FUP: Follow-up visit 1
  RND: Randomization visit
  SCR1, 2: Screening visit 1, 2
  T1, 2, 3, 4, 5, 6: Treatment visit 1, 2, 3, 4, 5, 6
  B: Break period, duration depending on group allocation
  TP1, 2: Treatment period 1, 2

In this study, estradiol levels were measured
  Treatment Visit 3 (corresponding to the end of 12 weeks treatment),
  Treatment Visit 6 (corresponding to the end of 24 weeks treatment).
Results:
Overall, estradiol levels under treatment were moderately suppressed compared to baseline. A trend of decreasing unbound estradiol concentrations with increasing Compound 1 exposure was noted, see Table 5. After the EoT, the Mean estradiol values returned to baseline levels for all Doses, data not shown.

Thus, Estradiol levels under treatment were moderately suppressed compared to baseline, but individual values remained mostly within the physiological follicular phase range. Overall, no safety concerns were identified from the data analysed.

TABLE 5

Study 17541 Estradiol concentrations in serum

| Cp1 Dose Group | Visit Day | Number of Subjects (N) | Mean pg/mL | SD pg/mL | Min pg/mL | Median pg/mL | Max pg/mL |
|---|---|---|---|---|---|---|---|
| 2 mg | Baseline | 34 | 135.97 | 138.76 | 29.4 | 93.55 | 644.2 |
|  | Treatment Visit 3 | 31 | 77.46 | 105.41 | 11.0 | 47.50 | 557.5 |
|  | Treatment Visit 6 | 31 | 44.69 | 30.81 | 7.9 | 42.50 | 132.5 |

SD: Standard Deviation
Cp1: Compound 1

Example 7: Hot Flush Events in Study Subject Treated with Compound 1 (Cp1)

See full study description in Example 6.

Hot flush events were reported and monitored during treatment.

Results:

Overall, no more than 11.4% of the subjects show hot flush, see Table 6.

TABLE 6

Hot flush events

| Dose Cp1 | Number of subjects (N) 100% | Number of subjects (N) | Events (%) |
|---|---|---|---|
| 2.0 mg | 30 | 4 | 11.4 |

Cp1: Compound 1

FIG. 1: 15818 Study design
FIG. 2: 15788 Study design
FIG. 3: 17541 Study design

The invention claimed is:

1. A method comprising administering (11β,17β)-17-Hydroxy-11-[4-(methylsulphonyl)phenyl]-17-(pentafluoroethyl)estra-4,9-dien-3-one (Compound 1) of formula (I)

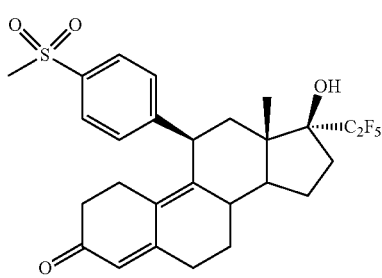

or a tautomer, or a pharmaceutically acceptable salt thereof, or a mixture of the foregoing, to a woman at a daily dosage of 1 mg to 5 mg for twelve (12) weeks to twenty-four (24) weeks for the treatment of one or more disorders associated with decreased estrogen selected from the group consisting of vulvar and vaginal atrophy, vaginal dryness, pruritus, dyspareunia, vasomotor instability manifested as hot flushes, and loss of bone mineral density, wherein the disorders associated with decreased estrogen are observed during administration of an SPRM other than Compound 1 but are reduced with administration of Compound 1 compared with administration of the SPRM other than Compound 1.

2. A method comprising administering (11β,17β)-17-Hydroxy-11-[4-(methylsulphonyl)phenyl]-17-(pentafluoroethyl)estra-4,9-dien-3-one (Compound 1) of formula (I)

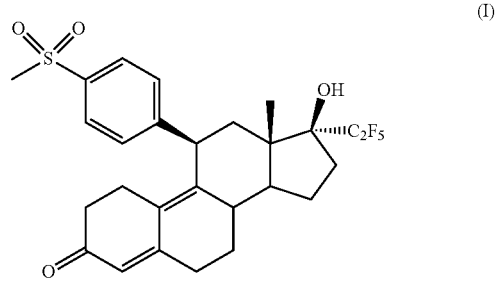

or a tautomer, or a pharmaceutically acceptable salt thereof, or a mixture of the foregoing, to a woman having endometriosis or uterine fibroids, at a daily dosage of 1 mg to 5 mg for twelve (12) weeks to twenty-four (24) weeks, wherein the woman is at risk of developing one or more disorders associated with decreased estrogen selected from the group consisting of vulvar and vaginal atrophy, vaginal dryness, pruritus, dyspareunia, vasomotor instability manifested as hot flushes, and loss of bone mineral density, and wherein Compound 1 regulates the concentration of circulating endogenous estradiol in the woman to a level within the range of 40 pg/mL to 85 pg/mL during treatment with Compound 1, and wherein the one or more disorders is reduced.

3. The method according to claim 1, wherein the daily dosage is of about 2 mg to 4 mg of Compound 1.

4. The method according to claim 1, wherein the treatment period includes at least one break period where administration of Compound 1 is discontinued until one (1) or two (2) menstrual bleeding episodes occur, and wherein the treatment period and break period are repeated at least one (1) time.

5. The method according to claim 1, wherein the woman was previously being treated for endometriosis with the SPRM other than Compound 1.

6. The method according to claim 1, wherein the woman was previously being treated for uterine fibroids (UF) with the SPRM other than Compound 1.

7. The method according to claim 1, wherein Compound 1 is administered to treat hot flushes and loss of bone mineral density.

8. The method according to claim 2, wherein the circulating endogenous estrogen is Estradiol (E2) (17β-estradiol).

9. The method according to claim 8 wherein the Estradiol (E2) is maintained to a level within the range of 70 to 85 pg/mL during treatment with Compound 1.

10. The method according to claim 7, wherein the hot flushes are mild- or moderate.

11. The method according to claim 1, wherein the SPRM other than Compound 1 is Ulipristal acetate (UPA) or is a Gonadotrophin-Releasing Hormone (GnRH) analogue selected from the group consisting of leuprolide and elagolix.

12. The method according to claim 2, wherein the SPRM other than Compound 1 is Ulipristal acetate (UPA) or is a Gonadotrophin-Releasing Hormone (GnRH) analogue selected from the group consisting of leuprolide and elagolix.

13. The method according to claim 11, wherein the SPRM other than Compound 1 is Ulipristal acetate (UPA).

14. The method according to claim 11, wherein the SPRM other than Compound 1 is Ulipristal acetate (UPA).

15. The method of claim 1, wherein Compound 1 is administered for twelve (12) weeks followed by one (1) menstrual bleeding episode.

16. The method of claim 4, wherein Compound 1 is administered for twenty-four (24) weeks followed by two (2) menstrual bleeding episodes.

17. A method comprising administering (11β,17β)-17-Hydroxy-11-[4-(methylsulphonyl)phenyl]-17-(pentafluoroethyl)estra-4,9-dien-3-one (Compound 1) of formula (I)

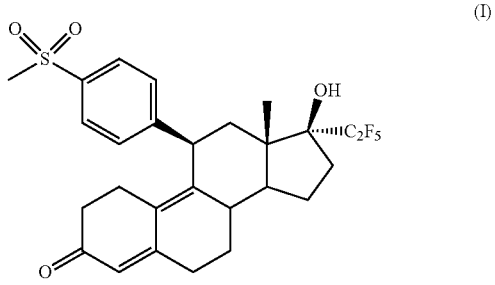

(I)

or a tautomer, or a pharmaceutically acceptable salt thereof, or a mixture of the foregoing, to a woman at a daily dosage of 1 mg to 5 mg for twelve (12) to twenty-four (24) weeks for the treatment of at least one disorder associated with decreased estrogen selected from the group consisting of vulvar and vaginal atrophy, vaginal dryness, pruritus, dyspareunia, vasomotor instability manifested as hot flushes, and loss of bone mineral density, wherein the woman was previously treated for Endometriosis or Uterine Fibroids (UF) with ulipristal acetate (UPA), or a Gonadotrophin-Releasing Hormone (GnRH) analogue selected from the group consisting of leuprolide and elagolix, and exhibited a decreased circulating endogenous estradiol concentration in blood plasma during treatment with the ulipristal acetate (UPA), leuprolide or elagolix, and wherein the woman experienced at least one disorder associated with decreased estrogen upon treatment with the ulipristal acetate (UPA), leuprolide or elagolix.

18. The method according to claim 17, wherein the treatment includes at least one break period wherein administration of Compound 1 is discontinued until one (1) or two (2) menstrual bleeding episodes occur, and wherein the treatment period and break period are repeated at least one (1) time.

19. The method according to claim 18, wherein Compound 1 is administered for twelve (12) weeks followed by one (1) menstrual bleeding episode.

20. The method according to claim 18, wherein Compound 1 is administered for twenty-four (24) weeks followed by two (2) menstrual bleeding episodes.

* * * * *